United States Patent [19]

Kosal

[11] Patent Number: 5,208,074
[45] Date of Patent: May 4, 1993

[54] SOLUBLE ALKALI METAL STEARATE SOLUTION COMPOSITIONS

[75] Inventor: Jeffrey A. Kosal, Midland, Mich.

[73] Assignee: Dow Corning Corporation, Midland, Mich.

[21] Appl. No.: 803,888

[22] Filed: Dec. 9, 1991

[51] Int. Cl.$^5$ .............................................. B05D 3/02
[52] U.S. Cl. ............................... 427/389; 106/215; 106/243; 106/244; 252/8.57; 252/8.6; 252/8.9; 424/70; 427/389.9; 428/263; 428/473
[58] Field of Search ................... 106/215, 243, 244; 252/8.57, 8.6, 8.9; 424/70; 427/389, 389.9; 428/263, 473

[56] References Cited

U.S. PATENT DOCUMENTS

| | | | |
|---|---|---|---|
| 3,914,519 | 10/1975 | Hall et al. | 428/457 |
| 4,532,132 | 7/1985 | Keil | 514/772 |
| 4,556,495 | 12/1985 | Shaw | 252/8.55 X |
| 4,948,578 | 8/1990 | Burger et al. | 424/DIG. 5 |
| 5,062,973 | 11/1991 | Kellett | 427/242 X |

*Primary Examiner*—Michael Lusigan
*Attorney, Agent, or Firm*—Jim L. DeCesare

[57] ABSTRACT

This invention relates to solutions of alkali metal stearates which remain soluble and stable at room temperature. In particular, the invention relates to an aqueous solution which includes an alkali metal stearate selected from the group consisting of sodium stearate and potassium stearate, and a water soluble nonionic surfactant. More particularly, the invention relates to a solution which when deposited on a substrate forms a stearate-surfactant lubricant layer upon removal of water. The solutions may be used in neat form or delivered as part of an emulsion.

5 Claims, No Drawings

SOLUBLE ALKALI METAL STEARATE SOLUTION COMPOSITIONS

BACKGROUND OF THE INVENTION

This invention relates to solutions of alkali metal stearates which remain soluble and stable at room temperature. In particular, the invention relates to an aqueous solution which includes an alkali metal stearate selected from the group consisting of sodium stearate and potassium stearate, and a water soluble nonionic surfactant. More particularly, the invention relates to a solution which when deposited on a substrate forms a stearate-surfactant lubricant layer upon removal of water. The solutions may be used in neat form or delivered as part of an emulsion.

Alkali metal stearates are blends of an alkali metal and stearic acid, also known as octadecanoic acid, and palmitic acid, also known as hexadecanoic acid. Alkali metal stearates have found a wide use in many product applications. Stearates typically have a "slippery" feel to them which is why they are used in some cases as lubricants and release agents. Stearates are also used as gelling agents, surfactants, thickeners and solidifiers. Generally, 3 to 10 percent of sodium stearate yields sticks having a degree of firmness particularly suitable for deodorant sticks. The mechanism behind stearate solidification and thickening is mentioned in the CRC Handbook of Lubrication pg. 55 as the formation of stearate fibers in solution.

Of all the alkali metal stearates, the sodium and potassium stearates are the only ones that have any water solubility associated with them, all other stearates are essentially water insoluble. However, sodium and potassium stearate are soluble only in water at a temperature about 70° C. At temperatures approaching room temperature, such sodium and potassium stearate solutions become unstable and flocculate out of solution. For example, solutions of sodium and potassium stearate with levels as low as 0.7% sodium and potassium stearate solids become soluble in water heated to 70° C. but upon cooling to room temperature, the solution gels completely.

Accordingly, the need exits for an aqueous solution of alkali metal stearates which is soluble and stable at room room temperature. The term "stable" is defined to mean that no precipitate or gel forms for a period in excess of 90 days.

SUMMARY OF THE INVENTION

It is an object of the present invention to provide a alkali metal stearate solution composition which is free of the defects and deficiencies of the prior art.

It is another object of the present invention to provide a alkali metal stearate solution composition which is soluble and stable at room temperature.

It is a further object of this invention to provide a alkali metal stearate solution composition which when deposited on a substrate forms a stearate-surfactant lubricant layer.

These and other objects are realized by the aqueous alkali metal stearate solution compositions of this invention which comprise (A) an alkali metal stearate selected from the group consisting of sodium stearate, potassium stearate and mixtures thereof;

(B) a water soluble nonionic surfactant having the general formula $$C_aH_b(OCH_2CH_2)_nOH$$

wherein:
a is an integer from 11 to 15,
b is an integer from 23 to 31, and
n is an integer with a average value of from 4 to 10; and
(C) water;
wherein the surfactant (B) is present in at least a 1:1 weight ratio with the alkali metal (A).

DETAILED DESCRIPTION OF THE INVENTION

The present invention relates to an alkali metal stearate solution which is stable at room temperature. The solution compositions of the present invention may also be formulated into emulsions.

Component (A) of the present invention is sodium stearate, potassium stearate or mixtures thereof. Sodium stearate and potassium stearate are well known in the art and are commercially available. The various quantities of impurities found in the commercially available samples of sodium stearate and potassium stearate such as sodium palmitate have not been shown to deleteriously effect the compositions of the present invention. Preferred stearates include the sodium stearates commercially available as Grade T-1 from Witco Chemical Corp., New York, N.Y. However, useful stearate salts can be formed in situ in the mixture of ingredients from which the alkali metal is formed, by neutralizing stearic acid with a base such as an alkali metal hydroxide, e.g., KOH or NaOH.

The alkali metal stearate, component (A), is present in an amount of from 0.01 to 10 weight percent of the composition. Preferably, the alkali metal stearate is present in an amount of from 0.8 to 4.0 weight percent of the composition.

Component (B) is a water soluble nonionic surfactant having the general formula $$C_aH_b(OCH_2CH_2)_nOH$$

wherein: a is an integer from 11 to 15; b is an integer from 23 to 31; and n is an integer with a average value of from 4 to 10. The amount of component (B) has been determined to be critical. Surfactant (B) must be present in at least a 1:1 weight ratio with the alkali metal stearate, component (A). The preferred amount of component (B) has been found to depend on the amount of alkali metal stearate, component (A), in the solution and the type of water soluble nonionic surfactant, component (B), used. Water soluble nonionic surfactants which meet this formula are well known in the art and are commercially available. Preferred water soluble nonionic surfactants include Tergitol ® TMN-6 and Tergitol ® 15-S-9 which can be obtained from Union Carbide Corporation, Danbury, Conn. Tergitol ® TMN-6 is polyoxyethylene (6) isolauryl ether. Tergitol ® 15-S-9 is a polyethylene glycol ether of a mixture of synthetic C11–C15 fatty alcohols with an average of 9 moles of ethylene oxide.

The third component (C) of the present invention is water which includes tap water and deionized water. Deionized water is preferred since a slight haziness may appear in solutions containing tap water. The haziness is due to the formation of very small crystals that within 24 hours settle to the bottom of the container. These crystals are believed to be calcium and magnesium stearates formed as a result of using hard water.

The water, component (C), may optionally contain an electrolyte. Any electrolyte may be used as long as the pH of the solution is maintained at 6.5 or above. If the pH drops below 6.5, the sodium stearate and potassium stearate may convert to stearic acid and precipitate. It is important to note that certain electrolytes are preferred. Electrolytes which are known to accelerate the thickening mechanism of sodium and potassium stearate, such as sodium chloride, are not recommended. Preferred electrolytes include sodium hydroxide, pottasium hydroxide and sodium borate. Such preferred electrolytes act as buffers and maintains the solution at a pH of about 9.0-12. The solution compositions of the present invention are prepared by combining water, a nonionic surfactant and optionally an electrolyte to form a solution. The solution is heated to between 65° C. to 95° C. At some point during the heating of the solution, the sodium or potassium stearate is added while the solution is agitated. Suitable means for agitation include a spatula, a magnetic stir bar and a mechanical stirrer. Agitation is continued and the temperature of the solution is maintained at between 65° C. and 90° C. for between five to ninety minutes. The solution is allowed to cool to room temperature.

The solution composition obtained by the method of the present invention is applied to the surface of a substrate. After the water is removed, by warming on a hot plate or by evaporation at room temperature, a sodium stearate-surfactant film is formed.

By choice of the proper formulation and application conditions including the optional use of an electrolyte, the solution compositions can be applied and will adhere to substantially all solid substrates. Substrates which are especially contemplated herein are skin, hair, textiles, plastics, glasses, woods, painted surfaces, leather, ceramics, paper and metals. For example, the compositions of the present invention may be applied to the skin, i.e., the arms, the legs, the entire body, where moisturizing or treatment is desired. The compositions of the present invention may also be used as release agents.

In order that those skilled in the art may better understand how to practice the present invention, the following examples are given by way of illustration and not by way of limitation. All parts and percentages in the examples are on a weight basis.

A. Evaluation of critical combinations:

EXAMPLE I

Deionized water, 99.39 grams was heated to 60° C. Next, 0.61 grams of sodium stearate was added while agitation was applied. Agitation was continued and the solution was heated to 85° C. The temperature of the solution was maintained at 85° C. for ten minutes. The solution was poured into a glass jar and allowed to air cool to 20° C. The solution was stored at 20° C. The solution gelled within four hours.

EXAMPLE II

A solution of 98.49 grams of deionized water and 0.90 grams of sodium chloride, was prepared. The solution was heated to 60° C. Next, 0.61 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The solution was stored at 20° C. The solution gelled within four hours.

EXAMPLE III

A solution of 96.24 grams of deionized water, 2.25 grams of polyoxyethylene (6) isolauryl ether and 0.90 grams of sodium chloride, was prepared. The solution was heated to 60° C. Next, 0.61 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The solution was stored at 20° C. Flocculation of the solution occured after four days and within two weeks the solution gelled.

EXAMPLE IV

A solution of 97.14 grams of deionized water and 2.25 grams of polyoxyethylene (6) isolauryl ether, was prepared. The solution was heated to 60° C. Next, 0.61 grams of sodium stearate was added while the solution underwent agitation. Agitation was continued and the solution was heated to 85° C.

The temperature of the solution was maintained at 85° C. for ten minutes. The solution was poured into a glass jar and allowed to air cool to 20° C., at which temperature the solution was stored. The solution remained clear in excess of 90 days. The solution was applied to a glass and a metal substrate. The water in the solution was allowed to evaporate at room temperature. A sodium stearate-surfactant film remained on the substrate.

The solution was further evaluated for its ability to remain soluble at reduced temperatures. Ten grams of the solution was added to a ½ ounce glass vial. The glass vial was capped and placed into a refrigerated bath at 15° C. After 1.5 hours, the solution remained clear. The temperature of the bath was further lowered to 10° C. After one hour, the solution became slightly hazy. The temperature of the bath was further lowered to 5° C. After 15 minutes, the solution remained slightly hazy. The glass vial was removed from the bath and the solution was allowed to warm to room temperature. Upon warming to room temperature, the solution became clear. The solution was applied to a glass and a metal substrate. The water in the solution was allowed to evaporate at room temperature. A sodium stearate-surfactant film remained on the substrate.

B. Evaluation of various electrolytes:

EXAMPLE V

A solution of 97.14 grams of deionized water and 2.25 grams of polyoxyethylene (6) isolauryl ether, was prepared. The solution was heated to 60° C. Next, 0.61 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The pH of the solution was measured to be 8.0. The solution was stored at 20° C. The solution remained clear in excess of 90 days.

EXAMPLE VI

A solution of 96.24 grams of deionized water, 2.25 grams of polyoxyethylene (6) isolauryl ether and 0.90 grams of sodium hydroxide was prepared. The solution was heated to 60° C. Next, 0.61 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The pH of the solution was measured to be 11.5. The solution was stored at 20° C. The solution remained clear in excess of 90 days.

EXAMPLE VII

A solution of 96.24 grams of deionized water, 2.25 grams of polyoxyethylene (6) isolauryl ether and 0.90 grams of sodium borate, was prepared. The solution was heated to 60° C. Next, 0.61 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The solution was stored at 20° C. The pH of the solution was measured to be 9.0. The solution remained clear in excess of 90 days.

EXAMPLE VIII

A solution of 96.24 grams of deionized water, 2.25 grams of polyoxyethylene (6) isolauryl ether and 0.90 grams of sodium chloride, was prepared. The solution was heated to 60° C. Next, 0.61 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The solution was stored at 20° C. The pH of the solution was measured to be 8.0. Flocculation of the solution occured after four days and within two weeks the solution gelled.

C. Evaluation of surfactant level to stearate level:

EXAMPLE IX

A solution of 95.65 grams of deionized water, 2.25 grams of polyoxyethylene (6) isolauryl ether and 0.90 grams of sodium borate, was prepared. The solution was heated to 60° C. Next, 1.20 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The solution was stored at 20° C. The solution gelled within 24 hours.

EXAMPLE X

A solution of 93.50 grams of deionized water, 4.40 grams of polyoxyethylene (6) isolauryl ether and 0.90 grams of sodium borate, was prepared. The solution was heated to 60° C. Next, 1.20 grams of sodium stearate and added while the solution underwent agitation. Agitation was continued and the solution was heated at 85° C. The temperature of the solution was maintained at 85° C. for ten minutes. The solution was poured into a glass jar and allowed to air cool to 20° C. The solution was stored at 20° C. The solution remained clear in excess of 90 days. The solution was applied to a glass and a metal substrate. The water in the solution was allowed to evaporate at room temperature. A sodium stearate-surfactant film remained on the substrate.

EXAMPLE XI

A solution of 92.55 grams of deionized water, 4.40 grams of polyoxyethylene (6) isolauryl ether and 0.80 grams of sodium borate, was prepared. The solution was heated to 60° C. Next, 2.25 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The solution was stored at 20° C. The solution gelled within two hours.

EXAMPLE XII

A solution of 88.65 grams of deionized water, 8.30 grams of polyoxyethylene (6) isolauryl ether and 0.80 grams of sodium borate, was prepared. The solution was heated to 60° C. Next, 2.25 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The solution was stored at 20° C. The solution remained clear in excess of 90 days. The solution was applied to a glass and a metal substrate. The water in the solution was allowed to evaporate at room temperature. A sodium stearate-surfactant film remained on the substrate.

D. Evaluation of deionized and tap water:

EXAMPLE XIII

A solution of 95.65 grams of tap water, 2.25 grams of polyoxyethylene (6) isolauryl ether and 0.90 grams of sodium borate, was prepared. The solution was heated to 60° C. Next, 1.20 grams of sodium stearate was added while the solution underwent agitation. Agitation was continued and the solution was heated to 85° C. The sodium stearate dissolved at about 68° C., however, a slight haziness was noticed in the solution. The temperature of the solution was maintained at 85° C. for ten minutes. The solution was poured into a glass jar and allowed to air cool to 20° C. The solution was stored at 20° C. The solution gelled within 24 hours.

EXAMPLE XIV

A solution of 93.50 grams of tap water, 4.40 grams of polyoxyethylene (6) isolauryl ether and 0.90 grams of sodium borate, was prepared. The solution was heated to 60° C. Next, 1.20 grams of sodium stearate was added while the solution underwent agitation. Agitation was continued and the solution was heated to 85° C. The sodium stearate dissolved at about 68° C., however, a slight haziness was noticed in the solution. The temperature of the solution was maintained at 85° C. for ten minutes. The solution was poured into a glass jar and allowed to air cool to 20° C. The solution was stored at 20° C. The solution remained clear in excess of 90 days. The solution was applied to a glass and a metal substrate. The water in the solution was allowed to evaporate at room temperature. A sodium stearate-surfactant film remained on the substrate.

E. Evaluation of various surfactants:

EXAMPLE XV

A solution of 88.65 grams of deionized water, 8.3 grams of a polyethylene glycol ether of a mixture of synthetic C11–C15 fatty alcohols with an average of 9 moles of ethylene oxide, and 0.80 grams of sodium borate, was prepared. The solution was heated to 60° C. Next, 2.25 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The solution was stored at 20° C. The solution remained clear in excess of 90 days.

EXAMPLE XVI

A solution of 88.65 grams of deionized water, 8.3 grams of $C_{12}H_{25}(OCH_2CH_2)_n$, where n has an average value of 10, and 0.80 grams of sodium borate, was prepared. The solution was heated to 60° C. Next, 2.25 grams of sodium stearate was added while the solution underwent agitation. Agitation was continued and the solution was heated to 85° C. The temperature of the solution was maintained at 85° C. for ten minutes. The solution was poured into a glass jar and allowed to air cool to 20° C. The solution was stored at 20° C. The solution gelled within four hours.

EXAMPLE XVII

A solution was prepared as in Example XVI except that the surfactant was replaced with Tergitol ® 15-S-7 which is a polyethylene glycol ether of a mixture of synthetic C11–15 fatty alcohols with an average of 7 moles of ethylene oxide. Tergitol ® 15-S-7 is available from Union Carbide Corporation, Danbury, CN. The solution gelled within four hours.

EXAMPLE XVIII

A solution was prepared as in Example XVI except that the surfactant was replaced with Tergitol ® 15-S-12 which is a polyethylene glycol ether of a mixture of synthetic C11–15 fatty alcohols with an average of 12 moles of ethylene oxide. Tergitol ® 15-S-12 is available from Union Carbide Corporation, Danbury, CN. The solution gelled within twenty-four hours.

EXAMPLE XIX

A solution was prepared as in Example XVI except that the surfactant was replaced with Tergitol ® 15-S-15 which is a nonionic polyethylene glycol ether of a mixture of synthetic C11–15 fatty alcohols with an average of 15 moles of ethylene oxide. Tergitol ® 15-S-15 is available from Union Carbide Corporation, Danbury, CN. The solution gelled within twenty-four hours.

EXAMPLE XX

A solution was prepared as in Example XVI except that the surfactant was replaced with Tergitol ® NP-6 which is a liquid nonionic ethoxylated nonylphenol with an HLB of 10.9. Tergitol ® NP-6 is available from Union Carbide Corporation, Danbury, CN. The solution gelled within twenty-four hours.

EXAMPLE XXI

A solution was prepared as in Example XVI except that the surfactant was replaced with Emulphogene ® DA-639 which is a liquid nonionic decyloxypoly(ethyleneoxy)ethanol. Emulphogene ® DA-639 is available from Rhone-Poulenc Chemical Company, Monmouth Junction, NJ. The solution gelled within twenty-four hours.

EXAMPLE XXII

A solution was prepared as in Example XVI except that the surfactant was replaced with Neodol ® 45-7T which is a nonionic $C_{14}$–$C_{15}$ linear primary alcohol ethoxylate containing an average of 7.9 moles of ethylene oxide per mole of alcohol, and has an HLB of 12.3. Neodol ® 45-7T is available from Shell Chemical Company, Houston, TX. The solution gelled within twenty-four hours.

EXAMPLE XXIII

A solution was prepared as in Example XVI except that the surfactant was replaced with Tergitol ® 15-S-5 which is a liquid nonionic $C_{11}$–$C_{15}$ secondary alcohol ethoxylate with an HLB of 10.5. Tergitol ® 15-S-5 is available from Union Carbide Corporation, Danbury, CN. The solution gelled immediately.

EXAMPLE XXIV

A solution was prepared as in Example XVI except that the surfactant was replaced with a silicone glycol having the formula $$(CH_3)_3Si-O-\underset{\underset{(CH_2)_3(OCH_2CH_2)_7OH}{|}}{\overset{\overset{CH_3}{|}}{Si}}-O-Si(CH_3)_3$$

The solution gelled within one hour.

EXAMPLE XXV

A solution was prepared as in Example XVI except that the surfactant was replaced with a silicone glycol having the formula $$(CH_3)_3Si-O-\underset{\underset{(CH_2)_3(OCH_2CH_2)_{12}OH}{|}}{\overset{\overset{CH_3}{|}}{Si}}-O-Si(CH_3)_3$$

The solution gelled within one hour.

F. Evaluation of alcohol solutions as an alternative:

EXAMPLE XXVI

In this example, the water used in the above examples was replaced with ethyl alcohol. Borax was not included in the formulation since borax is insoluble in alcohol.

A solution of 89.40 grams of ethyl alcohol U.S.P. 190 and 8.35 grams of polyoxyethylene (6) isolauryl ether, was prepared. The solution was heated to 60° C. Next, 2.25 grams of sodium stearate was added while the solution underwent agitation. Agitation was continued and the solution was heated to 70° C. The temperature of the solution was maintained at 70° C. for one hour, during which time samples were taken at 0, 15, 30, 45 and 60 minutes. All of the samples gelled upon cooling to 20° C.

G. Evaluation of Examples I–XXVI:

The examples clearly show that a water soluble nonionic surfactant having the general formula $$C_aH_b(OCH_2CH_2)_nOH$$

wherein: a is an integer from 11 to 15; b is an integer from 23 to 31; and n is an integer with a average value of from 4 to 10, is necessary to keep the alkali metal stearates soluble in solution. In addition, the examples indicate that the water soluble nonionic surfactant of the above formula must be present in at least a 1:1 weight ratio with the alkali metal stearates. Moreover, the examples illustrate that electrolytes, other than sodium chloride, may be used without effecting solution stability as long as the final pH of the solution is maintained at 6.5 or above.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

What is claimed is:

1. An aqueous alkali metal stearate solution comprising: 0.01–10.0 weight percent of an alkali metal stearate selected from the group consisting of sodium stearate, potassium stearate, and mixtures thereof; 0.01–20.0 weight percent of a water soluble nonionic surfactant having the formula $C_aH_b(OCH_2CH_2)_nOH$ in which a has a value of 11–15, b has a value of 23–31, and n has an average value of 4–10; and 70.0–99.98 weight percent of water; the surfactant being present in at least a 1:1 weight ratio with the alkali metal stearate; and an effective buffering amount of an electrolyte selected from the group consisting of sodium hydroxide, potassium hydroxide, and sodium borate; the pH of the solution being 6.5 or above.

2. The solution of claim 1 in which the surfactant is selected from the group consisting of polyoxyethylene (6) isolauryl ether, and a polyethylene glycol ether of a mixture of synthetic $C_{11}$–$C_{15}$ fatty alcohols with an average of nine moles of ethylene oxide.

3. A process for preparing a stearate-surfactant film on a substrate comprising applying the solution of claim 1 to a substrate, and removing water to form the film.

4. The process of claim 3 in which the solution is applied to a substrate selected from the group consisting of hair, skin, textile, and leather.

5. The solution of claim 1 in which the pH of the solution is 9–12.

* * * * *